United States Patent
Wang et al.

(10) Patent No.: US 10,099,977 B2
(45) Date of Patent: Oct. 16, 2018

(54) METHODS FOR REMOVING HALOGENATED ETHYLENE IMPURITIES IN 2, 3, 3, 3-TETRAFLUOROPROPENE PRODUCT

(71) Applicant: HONEYWELL INTERNATIONAL INC., Morristown, NJ (US)

(72) Inventors: Haiyou Wang, Amherst, NY (US); Hsueh Sung Tung, Getzville, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 15/267,599

(22) Filed: Sep. 16, 2016

(65) Prior Publication Data

US 2017/0001931 A1    Jan. 5, 2017

Related U.S. Application Data

(63) Continuation of application No. 14/206,026, filed on Mar. 12, 2014, now Pat. No. 9,447,004.

(60) Provisional application No. 61/792,669, filed on Mar. 15, 2013.

(51) Int. Cl.
| | |
|---|---|
| *C07C 21/18* | (2006.01) |
| *C07C 17/087* | (2006.01) |
| *C07C 17/25* | (2006.01) |
| *C07C 17/389* | (2006.01) |

(52) U.S. Cl.
CPC ............ *C07C 21/18* (2013.01); *C07C 17/087* (2013.01); *C07C 17/25* (2013.01); *C07C 17/389* (2013.01); *C07B 2200/09* (2013.01); *Y02P 20/582* (2015.11)

(58) Field of Classification Search
CPC ....... C07C 17/389; C07C 21/18; C07C 17/25; C07C 17/206; C09K 50/45; C09K 5/044
See application file for complete search history.

(56) References Cited

U.S. PATENT DOCUMENTS

| | | | |
|---|---|---|---|
| 5,233,107 | A | 8/1993 | Jansen |
| 7,084,315 | B2 | 8/2006 | Corr et al. |
| 7,638,660 | B2 | 12/2009 | Wang et al. |
| 8,067,650 | B2 | 11/2011 | Wang et al. |
| 8,252,964 | B2 | 8/2012 | Devic et al. |
| 2003/0157009 | A1 | 8/2003 | Corr et al. |
| 2009/0240090 | A1 | 9/2009 | Merkel et al. |
| 2010/0047189 | A1 | 2/2010 | Seeton et al. |
| 2010/0193347 | A1 | 8/2010 | Hulse et al. |
| 2011/0031436 | A1* | 2/2011 | Mahler ................ C07C 17/04 252/78.1 |
| 2011/0087055 | A1 | 4/2011 | Tirtowidjojo et al. |
| 2011/0172470 | A1 | 7/2011 | Hamasaki et al. |
| 2011/0270001 | A1 | 11/2011 | Ishihara et al. |
| 2012/0004475 | A1 | 1/2012 | Miller et al. |
| 2012/0065435 | A1 | 3/2012 | Nishiguchi et al. |
| 2012/0123172 | A1 | 5/2012 | Hibino et al. |
| 2012/0187331 | A1 | 7/2012 | Singh et al. |
| 2012/0203037 | A1 | 8/2012 | Sharratt et al. |
| 2012/0222448 | A1 | 9/2012 | Chaki et al. |

FOREIGN PATENT DOCUMENTS

| | | |
|---|---|---|
| CN | 101597209 A | 12/2009 |
| CN | 102076645 A | 5/2011 |
| CN | 102149659 A | 8/2011 |
| CN | 102307831 A | 1/2012 |
| CN | 102695692 A | 9/2012 |
| GB | 2 439 209 A | 12/2007 |
| GB | 2492847 A | 1/2013 |
| JP | 2003-533447 A | 11/2003 |
| JP | 2009-227675 A | 10/2009 |
| JP | 2011-520017 A | 7/2011 |
| JP | 2012-1495 A | 1/2012 |
| JP | 2013-508265 A | 3/2013 |
| WO | 01/83411 A1 | 11/2001 |
| WO | 2007/123786 A1 | 11/2007 |
| WO | 2008/012559 A1 | 1/2008 |
| WO | 2013/011291 A1 | 1/2013 |

OTHER PUBLICATIONS

First Office Action issued in Chinese Patent Application No. 201480015919.6 dated May 4, 2016 (in English and Chinese).
International Search Report and Written Opinion issued in International Application No. PCT/US2014/024467 dated Jul. 4, 2014.
Supplementary European Search Report issued in Application No. 14 76 7769 dated Oct. 7, 2016.
Second Office Action issued in Chinese Application No. 201480015919.6 dated Mar. 1, 2017 (in Chinese and English).
Notification of Reasons for Rejection dated Dec. 18, 2017 issued in Japanese Application No. 2016-501546.

* cited by examiner

*Primary Examiner* — Jafar F Parsa
(74) *Attorney, Agent, or Firm* — Scully Scott Murphy and Presser

(57) ABSTRACT

Disclosed is a composition comprised of at least one compound selected from 2,3,3,3-tetrafluoropropene, 1,3,3,3-tetrafluoro-1-propene and 1-chloro-3,3,3-trifluoropropene and halogenated impurity selected from the group consisting of HFO-1141 ($CH_2$=CHF), HCFO-1140 ($CH_2$=CHCl), and HCFO-1131 ($CH_2$=CFCl and/or trans/cis-CHF=CHCl) and combination thereof, said halogenated impurity being present in said composition in an amount of 50 ppm or less.

14 Claims, No Drawings

METHODS FOR REMOVING HALOGENATED ETHYLENE IMPURITIES IN 2, 3, 3, 3-TETRAFLUOROPROPENE PRODUCT

CROSS REFERENCE TO RELATED APPLICATION

This application is a continuation of U.S. patent application Ser. No. 14/206,026, filed on Mar. 3, 2014, and claims priority of U.S. application Ser. No. 61/792,699, filed on Mar. 15, 2013, the contents of both of which are incorporated herein.

FIELD OF THE INVENTION

This invention relates to methods for removing impurities included in fluorinated organic compounds, especially methods for removing unsaturated impurities included in fluorinated olefins, and even more particularly to methods for removing halogenated ethylene impurities included in 2,3,3,3-tetrafluoro-1-propene (HFO-1234yf), 1,3,3,3-tetrafluoro-1-propene (HFO-1234ze) and 1-chloro-3,3,3-trifluoro-1-propene (HFO-1233zd).

BACKGROUND

Certain hydrofluoroolefins (HFOs), such as tetrafluoropropenes (including 2,3,3,3-tetrafluoro-1-propene (HFO-1234yf), and 1,3,3,3-tetrafluoro-1-propene (HFO-1234ze) are now known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike most chlorofluorocarbons (CFCs) and hydrochlorofluorocarbons (HCFCs), most HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing these hydrofluoroolefins are among leading materials being developed for use in many of the aforementioned applications.

A manufacturing process for preparing one of the fluoroolefins, HFO-1234yf, is disclosed in U.S. Pat. No. 8,058,486, and uses 1,1,2,3-tetrachloropropene (HCO-1230xa) as starting raw material. The process consists of the following three steps: 1) HCO-1230xa+HF→2-chloro-3,3,3-trifluoropropene (HCFO-1233xf)+HCl in a vapor phase reactor charged with a solid hydrofluorination catalyst such as fluorinated chromia, 2) HCFO-1233xf+HF→2-chloro-1,1,1,2-tetrafluoropropane (HCFC-244bb) in a liquid phase reactor charged with a liquid hydrofluorination catalyst such as fluorinated $SbCl_5$, and 3) HCFC-244bb→HFO-1234yf in a vapor phase reactor.

The other fluoroolefins identified hereinabove are prepared similarly from different starting materials. Each of them is prepared from the dehydrochlorination of a hydrofluorocarbon, e.g. a fluoroalkane. More specifically, HFO-1234ze is formed from the dehydrochlorination of 1-chloro-3,3,3-trifluoropropane (244fa) in both the Z and E isomers. HFO-1233zd is prepared from the dehydrochlorination from 1,1-dichloro-3,3,3-trifluoro-1-propene (243fa) in both the Z and E isomers.

Unfortunately, this process for making fluoroolefin, e.g., HFO-1234yf, can lead to the generation of toxic and/or otherwise undesirable by-products, which are difficult to remove.

For example, one common method for removing impurities is via distillation. However, this method of removal is made difficult if the boiling point of the impurity is close to that of the final fluoroolefin products or if substance interactions bring otherwise dissimilar boiling compounds close together (for example azeotropes). Further, even after distillation, it is still possible that small quantities of undesirable impurities will remain.

As a result, there is a need to identify impurities generated in the process of making fluoroolefin, e.g., HFO-1234yf and methods for removing these impurities.

SUMMARY OF THE PRESENT INVENTION

The present inventors have unexpectedly found that the final HFO-1234yf, HFO-1234ze and HCFO-1233zd products, which were obtained after the distillation of HFO-1234yf, HFO-1234ze and HCFO-1233zd crude products, respectively still contained halogenated ethylene impurities. For example, the HFO-1234yf obtained after the dehydrochlorination step contained such halogenated ethylene impurities as HFO-1141 ($CH_2$=CHF), HCFO-1140 ($CH_2$=CHCl), and HCFO-1131 ($CH_2$=CFCl and/or trans/cis-CHF=CHCl). These halogenated ethylene impurities can be present in the fluoroolefin, e.g., HFO-1234yf, HFO-1234ze and HCFO-1233zd, product stream in an amount as much as 0.1% by weight, thereby reducing the concentration and purity of the respective fluoroolefins. Moreover, it is well known that HCFO-1140 is a carcinogenic agent. The toxicity of other halogenated ethylenes is unknown. Due to at least these reasons, it is undesirable for these halogenated ethylenes to be present in the HFO-1234yf final product. In addition, the presence of these halogenated ethylenes may cause detrimental impact on the efficiency of the production of fluoroolefins, such as HFO-1234yf, HFO-1234ze and HCFO-1233zd. Therefore, there is a need for means by which these unsaturated impurities can be removed or at least reduced from the HFO-1234yf product.

The present invention provides a method for removing halogenated ethylene impurities included in the fluoroolefin, e.g., HFO-1234yf product. Non-limiting examples of halogenated ethylenes comprise HFO-1141 ($CH_2$=CHF), HCO-1140 ($CH_2$=CHCl), and HCFO-1131 ($CH_2$=CFCl and/or trans/cis-CHF=CHCl). Other unsaturated impurities including HFO-1243zf ($CF_3CH$=$CH_2$), and HCFO-1233xf ($CF_3CCl$=$CH_2$) present in said fluoroolefins also can be removed or at least reduced together with halogenated ethylenes.

In one embodiment, the method comprises contacting the product stream comprising the fluoroolefin product and the halogenated ethylene impurities with a physical adsorption agent of high surface area. Non-limiting examples of such adsorption agents include silica, activated carbons, cross linked polymers, amorphous and semicrystalline s-PS (syndiotactic polystyrene), various zeolite molecular sieves (such as 4 A, 5 A, 13X, ZSM-5, zeolite Beta, zeolite USY, and the like), and combinations thereof.

In another embodiment, the method comprises contacting the product stream comprising the fluoroolefin product and said halogenated ethylene impurities with a chemisorption catalyst, which is a trivalent metal oxide, or oxyhalide, or halide, or combination thereof. In an embodiment, the metals are chromium, iron and aluminum Non-limiting examples of such chemisorption catalysts include bulk or supported chromium oxide, chromium oxychloride, chromium oxyfluoride, chromium chloride, chromium fluoride, aluminium oxide, aluminium oxychloride, aluminium oxyfluoride, aluminium chloride, aluminium fluoride, iron (III) oxide, iron (III) oxychloride, iron (III) oxyfluoride, ferric chloride, ferric fluoride, and various combinations of these. The useful supports include, but are not limited to, silica, alumina, and activated carbon. For metal oxide (chromium oxide, aluminium oxide, iron (III) oxide, or any combination of these) catalyst, a halogenation pre-treatment is conducted by using HCl or HF.

DETAILED DESCRIPTION OF THE INVENTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive and not to an exclusive or. For example, a condition A or B is satisfied by any one of the following: A is true (or present) and B is false (or not present), A is false (or not present) and B is true (or present), and both A and B is true (or present).

Also, use of "a" or "an" is employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "fluoroolefin", as used herein, means a molecule containing hydrogen, carbon, optionally chlorine, fluorine, and a carbon-carbon double bond.

The term "hydrofluoroolefin", as used herein, means a molecule containing hydrogen, carbon, fluorine, and a carbon-carbon double bond.

The term fluoroalkane, as used herein, refers to an alkane having two or more carbon atoms containing hydrogen, carbon, fluorine, chlorine, whereby a chlorine atom and a hydrogen atom are substituted on two adjacent carbon atoms.

As used herein, the term "halogenated ethylene" refers to an ethylene molecule wherein one or both carbon atoms are substituted by a halogen, such as fluorine or chlorine. For purposes of this invention, these halogenated ethylenes are impurities that are formed in the process of preparing HFO-1234yf, HFO-1234ze and HFO-1233zd products, especially during the dehydrochlorination step. The ethylene impurity compounds may have 1, 2, 3 or 4 halogens thereon. In certain embodiments, the ethylene impurity compounds have one or two halogen atoms substituted thereon. Examples include HFO-1141 ($CH_2=CHF$), HCO-1140 ($CH_2=CHCl$), and HCFO-1131 ($CH_2=CFCl$ and/or trans/cis-$CHF=CHCl$) and the like.

The term "adsorbent" refers to a material that has the ability to extract a substance from a gas, liquid or solid by causing the substance to adhere to the material without changing the properties thereof. In the present invention, the adsorbent is a material that can remove halogenated ethylenes from a gas or liquid stream comprised of the halogenated ethylenes and the HFO-1234yf product, whereby the adsorbent has functionality to facilitate its preferential combination with the halogenated ethylene molecules and/or a pore opening sufficiently large to allow the halogenated ethylene molecules to enter into its interior while excluding the fluoroolefin, such as HFO-1234yf, HFO-1234ze and HCFO-1233zd molecules. Examples of adsorbents include activated carbons, zeolites, silica, amorphous and semicrystalline syndiotactic polystyrene, cross-linked polymers, and the like.

HFO-1234ze may exist as one of two configurational isomers, E or Z. HFO-1234ze as used herein refers to the isomers, E-HFO-1234ze or Z-HFO-1234ze, as well as any combinations or mixtures of such isomers.

HCFO-1233zd also may exist as one of two configurational isomers, E or Z. HCFO-1233zd as used herein refers to the isomers, E-HCFO-1233zd or Z-HCFO-1233zd, as well as any combinations or mixtures of such isomers.

The term "dehydrochlorination", "dehydrochlorinating", or "dehydrochlorinated", as used herein, means a process during which hydrogen and chlorine on adjacent carbons in a molecule are removed.

The term "an elevated temperature", as used herein, means a temperature higher than room temperature.

The present invention relates to a process for removing at least one halogenated ethylene impurities from fluoroolefins, especially those fluoroolefins generated from the dehydrochlorination of a fluoroalkane. Although illustrated with respect to a few fluoroolefins, the process described herein is applicable for the removal of at least one halogenated ethylene impurity from a fluoroolefin, especially as a result of dehydrochlorination. For example, an embodiment of the present invention is directed to a process for purifying HFO-1234yf product that is prepared by the process described herein by reducing the amount of halogenated ethylenes that may be present therein. These impurities arise from the preparation of HFO-1234yf, such as from the dehydrohyrochlorination of HCFC-244bb. The use of the adsorbents and the chemisorption catalysts are illustrated with respect to the preparation of HFO-1234yf, but the present application is not so limited.

A process for preparing HFO-1234yf is described in U.S. Pat. No. 8,084,653, the contents of which are incorporated by reference. As described hereinabove, the preparation of HFO-1234yf generally includes at least three reaction steps, as follows:

(i) (CX₂=CCl—CH₂X or CX₃—CCl=CH₂ or CX₃—CHCl—CH₂X)+HF→2-chloro-3,3,3-trifluoropropene (HCFO-1233xf)+HCl in a vapor phase reactor charged with a solid catalyst;

(ii) 2-chloro-3,3,3-trifluoropropene (HCFO-1233xf)+HF→2-chloro-1,1,1,2-tetrafluoropropane (HCFC-244bb) in a liquid phase reactor charged with a liquid hydrofluorination catalyst; and (iii) 2-chloro-1,1,1,2-tetrafluoropropane (HCFC-244bb) →2,3,3,3-tetrafluoropropene (HFO-1234yf) in a vapor phase reactor, wherein X is independently selected from F, Cl, Br, and I, provided that at least one X is not fluorine.

Generally speaking, the starting material of the first reaction step may be represented by one or more chlorinated compounds according to Formulas I, II, and/or III:

CX₂=CCl—CH₂X  (Formula I)

CX₃—CCl=CH₂  (Formula II)

CX₃—CHCl—CH₂X  (Formula III)

wherein X is independently selected from F, Cl, Br, and I, provided that at least one X is not fluorine. In certain embodiments, these compounds contain at least one chlorine, a majority of X is chlorine, or all X is chlorine.

In the first step, such starting materials (which, in certain embodiments includes 1,1,2,3-tetrachloropropene (HCO-1230xa) and/or 1,1,1,2,3-pentachloropropane (HCC-240db) is reacted with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, heavy intermediates, HCFC-244bb, HFC-245cb (1,1,1,2,2-pentafluoropropane), or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to, chromium, aluminum, cobalt, manganese, nickel and iron oxides, hydroxides, halides, oxyhalides, inorganic salts thereof and their mixtures, any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082, the contents of which are incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to catalyze the reaction.

This first step of the reaction is not necessarily limited to a vapor phase reaction, as described above, but may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuously, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

The effluent from the reactor may be optionally processed to achieve desired degrees of separation and/or other processing. By way of non-limiting example, the product effluent may contain one or more impurities, such as, HCl, unconverted reactants, and/or other by-products. These products may be removed using standard methods known or otherwise discussed herein. HCl, for example, can be recovered by conventional distillation, or using water or caustic scrubbers, and the unreacted starting reagents isolated and recycled.

In the second step of the process for forming 2,3,3,3-tetrafluoropropene, HCFO-1233xf, is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, Group Vb metal halides, or combinations thereof. Non-exclusive examples of liquid phase fluorination catalysts are antimony halide, tin halide, tantalum halide, titanium halide, niobium halide, molybdenum halide, iron halide, fluorinated chrome halide, fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves passing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is fed to a second vapor phase reactor (dehydrochlorination reactor) to be dehydrochlorinated to make the desired product 2,3,3,3-tetrafluoropropene (HFO-1234yf). This reaction can either be non-catalytic or it can contain a catalyst that can catalytically dehydrochlorinate HCFC-244bb to make HFO-1234yf. In an embodiment, the vessel contains catalyst, for example a fixed or fluid catalyst bed, packed with a suitable dehydrohalogenation catalyst, with suitable means to heat the reaction mixture to about the desired reaction temperature.

The catalysts, if present, for the dehydrochlorination reaction may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Incoloy 825, Alloy 20, Hastelloy, Inconel 600, and Inconel 625. Catalysts that may be utilized in this step include activated carbon, stainless steel (e.g., SS 316), austenitic nickel-based alloys (e.g., Inconel 625), nickel, and in certain embodiments fluorinated 10% CsCl/MgO.

While it is contemplated that a wide variety of reaction temperatures may be used, depending on relevant factors such as the catalyst being used and the most desired reaction product, the reaction temperature for the dehydrohalogenation step ranges from about 200° C. to about 800° C. In an embodiment, the reaction ranges from about 300° C. to about 800° C., but, in another embodiment, it is conducted at a temperature from about 300° C., to about 500° C., for example, from about 400° C. to about 500° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum, and in certain embodiments, it ranges from about 1 to about 200 psia, for example, from about 1 to about 120 psia.

In certain embodiments, an inert diluent gas, such as nitrogen, may be used in combination with the other reactor feed(s). When such a diluent is used, HCFC-244bb comprises from about 50% to greater than 99% by weight based on the combined weight of diluent and HCFC-244bb.

It is to be noted that the effluent from the dehydrochlorination reactor in the aforementioned reaction may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used, HCl is removed as an aqueous solution. When a caustic solution is used, HCl is removed from the system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf. The reactor effluent may be fed to a caustic scrubber or to a distillation column to remove the byproduct of HCl to produce an acid-free organic product which, optionally, may undergo further purification using one or any combination of purification techniques that are known in the art.

In vapor-phase HCFC-244bb dehydrochlorination, HCFC-244bb feed, which can be formed from HCFO-1233xf hydrofluorination as described in U.S. 20090240090, the contents of which are incorporated herein by reference, is fed continuously to a vaporizer and the vaporized feed to a reactor. Due to incomplete conversion of HCFO-1233xf and its close boiling point to HCFC-244bb as well as the formation of azeotrope or azeotrope-like composition of HCFC-244bb and HCFO-1233xf under certain conditions, the separation of these two compounds is difficult. For this reason, the HCFC-244bb feed generally contains certain amount of HCFO-1233xf. The dehydrochlorination reaction may be carried out under conditions to attain a HCFC-244bb conversion of about 5% or higher, about 20% or higher, or about 30% or higher.

The inventors have surprisingly found the presence of halogenated ethylene impurities in HFO-1234yf produced via HCFC-244bb dehydrochlorination. Non-limiting examples of halogenated ethylenes comprise HFO-1141 ($CH_2$=CHF), HCO-1140 ($CH_2$=CHCl), and HCFO-1131 ($CH_2$=CFCl and/or trans/cis-CHF=CHCl), and the like. It is well known that HCO-1140 is a carcinogenic agent. The toxicity of other halogenated ethylenes is unknown. In addition, the presence of these halogenated ethylenes may cause detrimental impact on the efficiency of the HFO-1234yf production. Due to at least these reasons, it is undesirable for these halogenated ethylenes to be present in the HFO-1234yf final product. The present invention provides methods for removing said halogenated ethylenes from the HFO-1234yf product.

In addition, the inventors have surprisingly found the presence of halogenated ethylene impurities from the fluoroolefins formed from the dehydrochlorination of other fluoroalkanes. The present process also reduces the amount of at least one of those halogenated ethylene impurities and/or substantially removes at least one of those halogenated ethylene impurities from the fluoroolefins. Other unsaturated impurities such as $CF_3CCH$, HFO-1243zf ($CF_3CH$=$CH_2$), HFO-1234ze (trans/cis-$CF_3CH$=CHF), and HCFO-1233xf ($CF_3CCl$=$CH_2$) present in HFO-1234yf also can be removed or at least reduced together with halogenated ethylene impurities by the process described herein.

The product stream contains the fluoroolefin, e.g., HFO-1234yf, with the impurities, including the halogenated ethylenes. In some embodiments of this invention, the amount of the fluoroolefin, e.g., HFO-1234yf, present in the mixture is at least 50 wt % based on the total weight of the mixture. In some embodiments of this invention, the amount of fluoroolefin, e.g., HFO-1234yf, in the mixture is at least 70 wt % based on the total weight of the mixture. In some embodiments of this invention, the amount of fluoroolefin, e.g., HFO-1234f, in the mixture is at least 90 wt % based on the total weight of the mixture.

In one embodiment, the method comprises contacting the product stream comprising the fluoroolefin, e.g., HFO-1234yf, product and said halogenated ethylene impurities with an adsorbent of sufficiently high surface area to remove the halogenated ethylene impurities.

Non-limiting examples of such adsorption agents include activated carbons, cross linked polymers, amorphous and semicrystalline s-PS (syndiotactic polystyrene), silica, zeolite molecular sieves (such as 4 A, 5 A, AW-500, ZSM-5, 13X, zeolite beta, zeolite USY, and the like), and combinations thereof. One type of adsorbents is activated carbon. Various types of activated carbons can be utilized, such as powdered activated carbon, granular activated carbon and extruded activated carbon. The adsorption efficiency and adsorption capacity of the activated carbon depend upon the particle size of the activated carbon in a dynamic flow system. In an embodiment, the activated carbon has an average particle size range of about 0.005 millimeter to about 10 millimeters. In another embodiment, the activated carbon has an average particle size range of about 0.04 millimeter to about 5 millimeters. In another embodiment, the activated carbon has an average particle size range of about 0.1 millimeter to about 2 millimeters. The adsorption capacity of a given activated carbon may also be improved by removing the ash content of the carbon. This may be done by a standard technique such as acid wash.

The term "activated carbon" includes any carbon with a relatively high surface area such as from about 50 to about 3000 $m^2/g$ or from about 100 to about 2000 $m^2/g$ (e.g. from about 200 to about 1500 $m^2/g$ or about 300 to about 1000 $m^2/g$). The activated carbon may be derived from any carbonaceous material, such as coal (e.g. charcoal), nutshells (e.g. coconut) and wood. Any form of activated carbon may be used, such as powdered, granulated, extruded and pelleted activated carbon.

As used herein, the term "activated carbon" includes the activated carbon which has been modified (e.g. impregnated) by additives which modify the functionality of the activated carbon and facilitate its combination with the compounds it is desired to remove. Examples of suitable additives include metals or metal compounds, and bases.

Typical metals include transition, alkali or alkaline earth metals, or salts thereof. Examples of suitable metals include Na, K, Cr, Mn, Au, Fe, Cu, Zn, Sn, Ta, Ti, Sb, Al, Co, Ni, Mo, Ru, Rh, Pd and/or Pt and/or a compound (e.g. a halide, hydroxide, carbonate) of one or more of these metals. Alkali metal (e.g. Na or K) salts are currently a preferred group of additive for the activated carbon, such as halide, hydroxide or carbonate salts of alkali metals salts. Hydroxide or carbonate salts of alkali metals salts are bases. Any other suitable bases can be used, including amides (e.g. sodium amide).

The impregnated activated carbon can be prepared by any means known in the art, for example soaking the carbon in a solution of the desired salt or salts and evaporating the solvent.

Examples of suitable commercially available activated carbons include those available from Chemviron Carbon, such as Carbon 207C, Carbon ST1X, Carbon 209M and Carbon 207EA and Carbon ST1X. However, any activated carbon may be used with the invention, provided they are treated and used as described herein.

An activated carbon having a particle size range of 0.595 millimeters.times.1.68 millimeters (12.times.30 mesh) is available from the Calgon Corporation as Calgon PCB (Pittsburgh coconut based) carbon. Another activated carbon having a particle size range of 0.105 millimeters.times.0.595 millimeters (30.times.140 mesh) is available from the Calgon Corporation as Calgon PCB (Pittsburgh coconut based) carbon. Another activated carbon having a particle size range of 0.42 millimeters.times.1.68 millimeters (12.times.40 mesh) is available from the Calgon Corporation as Calgon CAL (bituminous coal based) carbon.

Another type of adsorbents is cross-linked polymers, which contain short side chains (cross links) that connect different polymer chains into a "network". A cross-link is a bond that links one polymer chain to another. Cross-linked polymers are usually insoluble (don't dissolve) in solvents because the polymer chains are tied together by strong covalent bonds. Other polymers are usually soluble (they dissolve) in one or more solvents because it is possible to separate the polymer chains which are not covalently linked.

Crosslinking can be accomplished by a heat induced reaction between the polymers and a crosslinking agent. Polymers may also be crosslinked by means of electron irradiation. Non-limiting examples of polymers that can be cross-linked include polyethylene, polypropylene, polystyrene, etc. Very high surface area materials based on cross-linking of swollen chloromethylated polystyrene were prepared via Friedel-Crafts alkylation reaction (J. Chromatogr. A, 2002, 965, 65-73). Porous polymer adsorbent having a $N_2$/BET specific surface area of 1466 $m^2/g$ was prepared from precursor polystyrene beads cosslinked with 2% divinylbenzene (Chem. Comm., 2006, 2670-72). Such polymers can be used in the present process.

Another type of adsorbents is s-PS or syndiotactic polystyrene. s-PS is a polymer which forms co-crystalline phases (both clathrate and intercalate) with several guest molecules. By suitable solvent-extraction procedures, the guest molecules can be easily removed resulting in the nanoporous δ form with a permanent cavity (J. Chem. Mater., 2001, 13, 1506). The δ-nanoporous crystalline phase of s-PS presents high ethylene solubility and low ethylene diffusivity (J. Mater. Chem., 2008, 18, 1046-1050), which makes it suitable for the removal of ethylene and the like. s-PS is available from Dow Chemical under trademark Questra.

Silica is another type of adsorbents that can be used to purify the HFO-1234yf and delete the halogenated ethylenes. The silica is present in the form of a gel, which is available commercially.

Aluminosilicate molecular sieves (zeolites) are a further group of adsorbents that may be used in the subject invention. Typically, the zeolites have pores having openings which are sufficiently large to allow the undesired compounds to enter into the interior of the zeolite whereby the undesired compounds are retained, whilst excluding the desired compound from entering the interior of the zeolite. The zeolites used are those zeolites having pores which have openings which have a size across their largest dimension in the ranges indicated hereinabove. Examples of zeolite that can be used include 4 A, 5 A, AW-500, ZSM-5, 13X, zeolite beta, zeolite USY, and the like.

By pore opening in this context, it is referring to the mouth of the pore by which the undesired compound enters the body of the pore, where it may be retained. The openings to the pores may be elliptically shaped, essentially circular or even irregularly shaped, but will generally be elliptically shaped or essentially circular. When the pore openings are essentially circular, they should have a diameter in the range of about 3 to about 10 Å across their smaller dimension. They can still be effective at adsorbing compounds provided that the size of the openings across their largest dimension is in the range of from about 4 to about 8 Å. Where the adsorbent has pores having elliptically shaped openings, which are below 6 Å across their smaller dimension, they can still be effective at adsorbing compounds provided that the size of the openings across their largest dimension is in the range of from about 4 to about 8 Å.

In the process described herein, the fluoroolefin, e.g., the HFO-1234yf is in admixture with at least one halogenated ethylene is contacted with an adsorbent or chemisorption catalyst, as defined here.

In one embodiment, the fluoroolefin, e.g., HFO-1234yf, in admixture with at least one halogenated ethylene is contacted with an absorbent. The contacting step in this invention can be carried out using well-known chemical engineering practices for scrubbing organic compounds, which includes continuous, semi-continuous or batch operations. In some embodiments of this invention, the contacting step can be carried out by passing a stream of gaseous or liquid mixture of the fluoroolefin, e.g., HFO-1234yf, and the halogenated ethylene impurities through a fixed bed comprised of the adsorbent, as defined herein, in a vessel. Stirring and agitation of the bed may be carried out through use of known methods. In some embodiments, the fluoroolefin, e.g., HFO-1234yf, formed from the above process containing the halogenated ethylene impurities is mixed with the bed of adsorbent described hereinabove in a vessel equipped with an agitator.

In some embodiments of the invention, the temperature during the contacting step is from about −20° C. to about 200° C., while in other embodiments, the temperature during the contacting step is from about 0° C. to about 100° C. In some embodiments, the temperature during the contacting step is from about 10° C. to about 60° C., while in some embodiments of this invention, the temperature during the contacting step is about room temperature.

The pressure during the contacting step is not critical and can be in the range of 1 psi to about 400 psi.

During the contacting step, the mixture of the fluoroolefin, e.g., HFO-1234yf, and at least one halogenated ethylene impurity is scrubbed with the adsorbent in the contacting vessel, and the halogenated impurity is removed. In some embodiments of this invention, the concentration of the at least one halogenated impurity in the mixture is reduced to 50 ppm or less. In some embodiments of this invention, the concentration of the at least one halogenated ethylene impurity in the mixture is reduced to 20 ppm or less. In some embodiments of this invention, the concentration of the at least one halogenated ethylene impurity in the mixture is reduced to 10 ppm or less. In some embodiments of this invention, the amount of the at least one halogenated ethylene impurity in the mixture is reduced at least about 20% by weight relative to the amount originally present. In some embodiments of this invention, the amount of the at least one halogenated ethylene impurity in the mixture is reduced at least about 50% by weight relative to the amount originally present. In some embodiments of this invention, the amount of the at least one halogenated ethylene impurity in the mixture is reduced at least about 80% by weight relative to the amount originally present.

The fluoroolefin, e.g., HFO-1234yf, having reduced concentration of the impurity obtained from the contacting step can be recovered using techniques well-known in the art, such as condensation or distillation. In some embodiments of this invention, the fluoroolefin, e.g., HFO-1234yf, obtained from the contacting step may be further purified by fractional distillation.

During the process of the present invention, the adsorbents eventually become saturated with the halogenated ethylenes, at which point the adsorbent will no longer effectively remove the contaminants from the hydrocarbon stream. When saturation occurs, the adsorbent materials must be either replaced or regenerated. To determine whether the adsorbents are saturated with halogenated ethylenes, the fluoroolefin, e.g., HFO-1234yf, streams before and after passing through the adsorber vessel are periodically analyzed by various means such as gas chromatography for the compositions of halogenated ethylenes present on the adsorbent. After reaching its saturation of adsorption of the halogenated ethylenes and other impurities, the spent absorption can be regenerated and then can be re-used. In an embodiment, the adsorbent is regenerated by passing a heated regeneration fluid stream comprised of a carrier gas, which is inert through the adsorbent bed, often in a countercurrent manner.

More specifically, the regeneration step constitutes removal of at least one of the halogenated ethylenes from the adsorbent by heating and purging with an inert carrier gas. Suitable carrier gases include, but are not limited to, inert gases such as $N_2$, Ar, He, and various combinations of these gases. Sufficient heat must be applied to raise the temperature of the adsorbent and the vessel to vaporize the liquid and offset the heat of wetting the adsorbent agent surface. Depending on the nature of the adsorbent agent, bed temperatures range from about 100 to about 400° C. For instance, 4 Å and 5 Å molecular sieves require a temperature in the 200-315° C. range. After regeneration, a cooling period is necessary to reduce the absorption agent temperature to within 15° C. of the temperature of the HFO-1234yf stream to be processed. This is most conveniently done by using the same gas stream as for heating, but with no heat input. In an embodiment, the gas flow is countercurrent to the gas flow during the heat cycle, and then in the same direction as in the gas flow during the heat cycle (relative to the process stream) during cooling. In this way the adsorbed contaminants are desorbed from the adsorbent and then removed by regenerated fluid stream, by which the contaminants are carried out of the bed.

Alternatively, small quantities of adsorption agent may be dried in the absence of a purge gas by oven heating followed by slow cooling in a closed drying system using a desiccant.

In an embodiment, the regeneration of the adsorbent occurs simultaneously with the purging of the halogenated impurities. In an embodiment, the HFO-12343yf stream is passed through one or more beds of adsorbent, as defined herein to remove halogenated ethylenes, while simultaneously regenerating a used bed at the high temperatures, as described hereinabove, to desorb the halogenated ethylenes. The heated bed is then cooled and is ready for another adsorption step.

In another embodiment, the method comprises contacting the product stream comprising the fluoroolefin, e.g., HFO-1234yf product, obtained from the process described herein, including the dehydrochlorination reaction, and said halogenated ethylene impurities with a chemisorption catalyst, which is a trivalent metal oxide, or oxyhalide, or halide, or combination thereof. Non-limiting examples of such chemisorption catalysts include chromium oxide, chromium oxychloride, chromium oxyfluoride, chromium chloride, chromium fluoride, aluminium oxide, aluminium oxychloride, aluminium oxyfluoride, aluminium chloride, aluminium fluoride, iron (III) oxide, iron (III) oxychloride, iron (III) oxyfluoride, ferric chloride, ferric fluoride, and various combinations of these, such as a mixture of one chromium compound with an aluminum compound identified hereinabove or a chromium compound with an iron compound identified hereinabove, or a mixture of an aluminum compound with an iron compound from the list hereinabove or a mixture of a chromium compound, aluminum compound and an iron compound from the list hereinabove or one or more of the chromium compounds, with one or more of the aluminum compounds and one or more of the iron compounds from the list hereinabove. These chemisorption catalysts may be supported or unsupported. The useful supports include, but are not limited to, silica, alumina, and activated carbon. For metal oxide (chromium oxide, aluminium oxide, iron (III) oxide, or any combination of these) catalyst, a halogenation pre-treatment is conducted by using HCl or HF.

In one embodiment, the process involves passing the halogenated ethylenes contained HFO-1234yf stream through a catalytic bed charged with the chemisorption catalyst under conditions effective to remove the halogenated ethylenes. Depending on the nature of the chemisorption catalyst used, the chemisorption temperature can vary from room temperature to 100° C. For instance, an HCl-pretreated 35 wt % $Cr_2O_3/\gamma-Al_2O_3$ catalyst requires a temperature range of 70-75° C.

The pressure during the contacting step is not critical and can be in the range of 1 psi to about 400 psi.

During the contacting step, the mixture of the fluoroolefin, e.g., 1234yf, and at least one halogenated ethylene impurity is scrubbed with a chemisorption catalyst, and the halogenated impurity is removed. In some embodiments of this invention, the concentration of the at least one halogenated impurity in the mixture is reduced to 50 ppm or less. In some embodiments of this invention, the concentration of the at least one halogenated ethylene impurity in the mixture is reduced to 20 ppm or less. In some embodiments of this invention, the concentration of the at least one halogenated ethylene impurity in the mixture is reduced to 10 ppm or less. In some embodiments of this invention, the amount of the at least one halogenated ethylene impurity in the mixture is reduced at least about 20% by weight relative to the amount originally present. In some embodiments of this invention, the amount of the at least one halogenated ethylene impurity in the mixture is reduced at least about 50% by weight relative to the amount originally present. In some embodiments of this invention, the amount of the at least one halogenated ethylene impurity in the mixture is reduced at least about 80% by weight relative to the amount originally present.

The fluoroolefin, e.g., 1234yf, having reduced concentration of the impurity obtained from the contacting step can be recovered using techniques well-known in the art, such as condensation or distillation. In some embodiments of this invention, the fluoroolefin, e.g., HFO-1234yf, obtained from the contacting step may be further purified by fractional distillation.

During the process of the present invention, the chemisorption catalyst eventually become saturated with the halogenated ethylenes, at which point the chemisorption catalyst will no longer effectively remove the contaminants from the hydrocarbon stream. When saturation occurs, the chemisorption catalyst must be either replaced or regenerated. To determine whether the chemisorption catalyst is saturated with halogenated ethylenes, the fluoroolefin, e.g., HFO-1234yf, streams before and after catalytic reactor are periodically analyzed by various means such as, for example, by gas chromatography, to determine the amount of halogenated ethylenes present on the chemisorption catalyst. When the chemisorption catalyst is saturated with the halogenated ethylenes, the spent chemisorption catalyst can be regenerated using techniques known in the art and then can be re-used.

In an embodiment, the chemisorption catalyst is regenerated by passing a heated regeneration fluid stream comprised of a carrier gas, which is inert through the adsorbent bed, often in a countercurrent manner.

More specifically, regeneration constitutes removal of at least one of the halogenated ethylenes from the chemisorptions catalyst by heating and purging with a regeneration fluid, such as an inert gas, such as nitrogen, helium or argon. Sufficient heat must be applied to raise the temperature of the chemosorption catalyst and the vessel to vaporize the liquid and offset the heat of wetting the adsorbent agent surface. The bed temperature is raised from about 200 to about 600° C., but in another embodiment, it ranges from about 300 to about 500° C., while in another embodiment, it ranges from about 350 to about 400° C. After regeneration, a cooling period is necessary to reduce the temperature to within 15° C. of the temperature of the HFO-1234yf stream to be processed. This is most conveniently done by using the same gas stream as for heating, but with no heat input. In an embodiment, the regeneration of the chemisorption catalyst involves passing the fluoroolefin, e.g., HFO-1234yf stream through the chemisorption catalyst under conditions effective to remove halogenated ethylenes, while simultaneously, regenerating a previously used chemisorption catalyst at a high temperature to restore the activity of the catalyst. The chemisorption catalyst is then cooled and is ready for another chemisorption step.

Regeneration of a chemisorption catalyst can also be carried out in continuous flow of an oxidizing agent. Such oxidizing agents include, but are not limited to, $H_2O$, $CO_2$, $O_2$, air, $O_3$, $Cl_2$, $N_2O$, and combinations of these. In certain embodiments, the regeneration is carried out at a temperature of from about 200° C. to about 600° C., while in another embodiment, it is carried out in a temperature of about 300° C. to about 500° C. In still another embodiment, it is carried out in a temperature of about 350° C. to about 400° C. In one embodiment, the oxidizing agent is diluted or provided in diluted form. Suitable diluents include inert gases such as $N_2$, Ar, and He. In one aspect of this embodiment, the oxidizing agent is oxygen and is diluted with nitrogen. The dilution can be as high as practically possible, for example, up to and including about 0.1% volume of oxidizing agent. In an embodiment, the concentration of oxidizing agent after dilution ranges from about 0.5 to about 21 vol %, while in another embodiment, it ranges from about 1 to about 5 vol %, and, in another embodiment, it ranges from about 2 to about 3 vol %.

Using the present process, in which the fluoroolefin, e.g., HFO-1234yf, admixed with at least one halogenated ethylene is contacted with an adsorbent or the chemisorption catalyst, as described herein, the amount of the halogenated ethylene in admixture with 1234yf is reduced considerably. Moreover, other impurities may be present in the stream comprised, in addition to the halogenated ethylene, including HFO-1243zf ($CF_3CH=CH_2$), and HCFO-1233xf ($CF_3CCl=CH_2$). In an embodiment, at least one of these additional impurities can be removed or at least reduced together with halogenated ethylenes.

Thus, an embodiment is directed to a process for removing at least one halogenated ethylene impurity admixed with a fluorolefin comprised of 2,3,3,3-tetrafluoro-1-propene, said process comprising: contacting said mixture comprised of said fluoroolefin and at least one halogenated ethylene impurity with at least one adsorbent or at least one chemisorption catalyst to reduce the concentration of said at least one halogenated ethylene impurity. Using the process described herein, another embodiment is directed to a process comprising:

(a) dehydrochlorinating 2-chloro-1,1,1,2-tetrafluoropropane to form a mixture comprising 2,3,3,3-tetrafluoropropene and at least one halogenated ethylene impurity;

(b) contacting a mixture comprising 2,3,3,3-tetrafluoropropene and at least one halogenated ethylene impurity with at least one adsorbent or at least one chemisorption catalyst to reduce the concentration of said at least one halogenated ethylene impurity; and (c) recovering 2,3,3,3-tetrafluoropropene having reduced concentration of said halogenated ethylene impurity.

Another embodiment is directed to the additional removal of other unsaturated impurities such as HFO-1243zf ($CF_3CH=CH_2$), HFO-1234ze (E/Z-$CF_3CH=CHF$), and HCFO-1233xf ($CF_3CCl=CH_2$).

A further embodiment is directed to a process for removing at least one halogenated ethylene impurity admixed with a fluorolefin comprised of 1,3,3,3-tetrafluoro-1-propene in either the E form or Z form, said process comprising: contacting said mixture comprised of said fluoroolefin and at least one halogenated ethylene impurity with at least one adsorbent or at least one chemisorption catalyst to reduce the concentration of said at least one halogenated ethylene impurity. Using the procedure described herein, another embodiment is to a process comprising: (a) dehydrochlorinating 1-chloro-1,3,3,3-tetrafluoropropane to form a mixture comprising 1,3,3,3-tetrafluoro-1-propene in either the E form or Z form and at least one halogenated ethylene impurity; (b) contacting a mixture comprising 1,3,3,3-tetrafluoropropene and at least one halogenated ethylene impurity with at least one adsorbent or at least one chemisorption catalyst to reduce the concentration of said at least one halogenated ethylene impurity; and (c) recovering 1,3,3,3-tetrafluoropropene having reduced concentration of said halogenated ethylene impurity. This process can also reduce other unsaturated impurities, such as HFO-1243zf ($CF_3CH=CH_2$), HCFO-1233zd (E/Z-$CF_3CH=CHCl$)), and HCFO-1233xf ($CF_3CCl=CH_2$).

Another embodiment is directed to a process or removing at least one halogenated ethylene impurity admixed with a fluorolefin comprised of 1-chloro-3,3,3-trifluoro-1-propene in either the Z- or E-form, said process comprising: contacting said mixture comprised of said fluoroolefin and at least one halogenated ethylene impurity with at least one adsorbent or at least one chemisorption catalyst to reduce the concentration of said at least one halogenated ethylene impurity. Using the procedure described herein, another embodiment is to a process comprising: (a) dehydrochlorinating 1,1-dichloro-3,3,3-trifluoropropane to form a mixture comprising 1-chloro-3,3,3-trifluoro-1-propene in either the Z- or E-form and at least one halogenated ethylene impurity; (b) contacting said mixture comprising 1-chloro-3,3,3-trifluoro-1-propene in either the Z- or E-form and at least one halogenated ethylene impurity with at least one adsorbent or at least one chemisorption catalyst to reduce the concentration of said at least one halogenated ethylene impurity; and recovering 1-chloro-3,3,3-trifluoro-1-propene having reduced concentration of said halogenated ethylene impurity. This process can also reduce other unsaturated impurities, such as HFO-1243zf ($CF_3CH=CH_2$), HFO-1234ze (E/Z-$CF_3CH=CHF$), and HCFO-1233xf ($CF_3CCl=CH_2$)

The following non-limiting examples illustrate the present invention.

EXAMPLE 1

Example 1 illustrates the use of granule activated carbon (GAC) as a physical absorption agent to remove halogenated ethylene impurities included in HFO-1234yf product. This example also illustrates the regeneration of spent GAC.

20 ml of granule activated carbon (GAC), which has a specific surface area of about 1200 $m^2/g$, is loaded into a cylindrical Inconel 625 tube reactor of ¾" diameter. The reactor is immersed into a 3-zone electrical furnace. Process temperatures are recorded using a multi-point thermocouple running through the catalyst bed of about 4" high. The purified HFO-1234yf contains 35 ppm of trans-$CHCl=CHF$ and 6 ppm of HCO-1140. The purified HFO-1234yf feed is fed to the reactor at a rate of 12 g/h after being vaporized. The reactor is kept at room temperature and 1 atm. Effluent gases are periodically analyzed be means of GC for the concentrations of trans-$CHCl=CHF$ and HCO-1140 at reactor outlet. The analysis results indicate no trans-$CHCl=CHF$ and HCO-1140 are detected within instrument detecting limit during the first 100 hours on stream.

After 3000 hours on stream, GC analysis shows the concentrations of trans-$CHCl=CHF$ and HCO-1140 at reactor outlet are almost the same as at reactor inlet, indicating the GAC reaches the saturation of absorption. A regeneration of the spent GAC is followed. The purified HFO-1234yf feed is stopped first and then nitrogen flow is started at a rate of 100 ml/min. After purging the spent GAC bed for 2 hours at room temperature, the bed temperature is gradually raised to 325° C. and is then kept at 325° C. for 10 hours. Afterwards, the power to the electrical furnace is stopped and the regenerated GAC bed is cooled to room temperature in the same nitrogen flow. The regenerated AC is then tested under the same condition as used for the fresh GAC. The analysis results show that no trans-$CHCl=CHF$ and HCO-1140 is detected within instrument detecting limit during the next 100 hours on stream.

EXAMPLE 2

Example 2 illustrates the use of 5 A molsieve as a physical absorption agent to remove halogenated ethylene impurities included in HFO-1234yf product. This example also illustrates the regeneration of spent of 5 A molsieve.

20 ml of 5 A molsieve pellets is loaded into a cylindrical Inconel 625 tube reactor of ¾" diameter. The reactor is immersed into a 3-zone electrical furnace. Process temperatures are recorded using a multi-point thermocouple running through the catalyst bed of about 4" high. The purified HFO-1234yf contains 35 ppm of trans-$CHCl=CHF$ and 6 ppm of HCO-1140. The purified HFO-1234yf feed is fed to the reactor at a rate of 12 g/h after being vaporized. The reactor is kept at room temperature and 1 atm. Effluent gases are periodically analyzed be means of GC for the concentrations of trans-$CHCl=CHF$ and HCO-1140 at reactor outlet. The analysis results indicate no trans-$CHCl=CHF$ and HCO-1140 are detected within instrument detecting limit during the first 100 hours on stream.

After 3000 hours on stream, GC analysis shows the concentrations of trans-CHCl=CHF and HCO-1140 at reactor outlet are almost the same as at reactor inlet, indicating the 5 A molsieve reaches the saturation of absorption. A regeneration of the spent 5 A molsieve is followed. The purified HFO-1234yf feed is stopped first and then nitrogen flow is started at a rate of 100 ml/min. After purging the spent 5 A molsieve bed for 2 hours at room temperature, the bed temperature is gradually raised to 275° C. and is then kept at 275° C. for 10 hours. Afterwards, the power to the electrical furnace is stopped and the regenerated 5 A molsieve bed is cooled to room temperature in the same nitrogen flow. The regenerated 5 A molsieve is then tested under the same condition as used for the fresh 5 A molsieve. The analysis results show that no trans-CHCl=CHF and HCO-1140 is detected within instrument detecting limit during the next 100 hours on stream.

EXAMPLE 3

Example 2 illustrates the use of ZSM-5 molsieve as a physical absorption agent to remove halogenated ethylene impurities included in HFO-1234yf product. This example also illustrates the regeneration of spent of ZSM-5 molsieve.

20 ml of ZSM-5 molsieve pellets is loaded into a cylindrical Inconel 625 tube reactor of ¾" diameter. The reactor is immersed into a 3-zone electrical furnace. Process temperatures are recorded using a multi-point thermocouple running through the catalyst bed of about 4" high. The purified HFO-1234yf contains 35 ppm of trans-CHCl=CHF, 15 ppm of $CH_2$=CFCl, and 6 ppm of HCO-1140. The purified HFO-1234yf feed is fed to the reactor at a rate of 12 g/h after being vaporized. The reactor is kept at room temperature and 1 atm. Effluent gases are periodically analyzed be means of GC for the concentrations of trans-CHCl=CHF, $CH_2$=CFCl and HCO-1140 at reactor outlet. The analysis results indicate no trans-CHCl=CHF, $CH_2$=CFCl and HCO-1140 are detected within instrument detecting limit during the first 100 hours on stream.

After 3000 hours on stream, GC analysis shows the concentrations of trans-CHCl=CHF, $CH_2$=CFCl and HCO-1140 at reactor outlet are almost the same as at reactor inlet, indicating the ZSM-5 molsieve reaches the saturation of absorption. A regeneration of the spent ZSM-5 molsieve is followed. The purified HFO-1234yf feed is stopped first and then nitrogen flow is started at a rate of 100 ml/min. After purging the spent ZSM-5 molsieve bed for 2 hours at room temperature, the bed temperature is gradually raised to 275° C. and is then kept at 275° C. for 10 hours. Afterwards, the power to the electrical furnace is stopped and the regenerated ZSM-5 molsieve bed is cooled to room temperature in the same nitrogen flow. The regenerated ZSM-5 molsieve is then tested under the same condition as used for the fresh ZSM-5 molsieve. The analysis results show that no trans-CHCl=CHF, $CH_2$=CFCl and HCO-1140 is detected within instrument detecting limit during the next 100 hours on stream.

EXAMPLE 4

Example 4 illustrates the use of 35 wt % $Cr_2O_3$/65 wt % γ-$Al_2O_3$, pretreated with 0.5 vol % HCl, as a chemisorption catalyst to remove halogenated ethylene impurities included in HFO-1234yf product and the regeneration of spent chromium oxide catalyst.

20 ml of ⅛" 35 wt % $Cr_2O_3$/65 wt % γ-$Al_2O_3$ catalyst pellets (is loaded into a cylindrical Inconel 625 tube reactor of ¾" diameter, which is immersed into a 3-zone electrical furnace. Process temperatures are recorded using a multi-point thermocouple running through the chromium oxide catalyst bed of about 4" high. The purified HFO-1234yf contains 11 ppm of trans-CHCl=CHF and 4 ppm of HCO-1140. The purified HFO-1234yf feed is fed to the reactor at a rate of 12 g/h after being vaporized. The reactor is kept at 75° C. and 1 atm. Effluent gases are periodically analyzed be means of GC for the concentrations of trans-CHCl=CHF and HCO-1140 at reactor outlet. The analysis results indicate no trans-CHCl=CHF and HCO-1140 are detected within instrument detecting limit during the first 100 hours on stream.

After 2000 hours on stream, GC analysis shows the concentrations of trans-CHCl=CHF and HCO-1140 at reactor outlet are almost the same as at reactor inlet, indicating the chromium oxide catalyst is no longer active for chemisorption of these halogenated ethylenes. A regeneration of the spent chromium oxide catalyst is followed. The purified HFO-1234yf feed is stopped first and then nitrogen flow is started at a rate of 100 ml/min. After purging the spent catalyst bed for 2 hours at 75° C., the bed temperature is gradually raised to 350° C. in 2% $O_2$/$N_2$ flow (100 ml/min) and is then kept at 350° C. for 10 hours. Afterwards, the 2% $O_2$/$N_2$ flow is switched to $N_2$ flow (100 ml/min) and the catalyst bed temperature is lowered to 75° C. The regenerated chromium oxide catalyst is then tested under the same condition as used for the fresh chromium oxide catalyst. The analysis results show no trans-CHCl=CHF and HCO-1140 is detected within instrument detecting limit during the next 100 hours on stream.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A composition comprised of 2,3,3,3-tetrafluoropropene and first halogenated impurity comprised of HCFO-1140 ($CH_2$=CHCl) said halogenated impurity being present in said composition in an amount greater than 0 ppm but less than or equal to 50 ppm, said 2,3,3,3-tetrafluoropropene being present in at least 90% by weight of said composition.

2. The composition according to claim 1 wherein said first halogenated impurity is present in said composition in an amount greater than 0 ppm but less than or equal to 20 ppm.

3. The composition according to claim 1 wherein said first halogenated impurity is present in said composition in an amount greater than 0 but less than or equal to 10 ppm.

4. The composition according to claim 1 wherein a second impurity selected from CF$_3$C≡CH, HFO-1243zf (CF$_3$CH═CH$_2$), HFO-1234ze (E/Z-CF$_3$CH═CHF), HCFO-1233zd (E/Z-CF$_3$CH═CHCl), HCFO-1233xf (CF$_3$CCl═CH$_2$) and combination thereof is additionally present.

5. The composition according to claim 2 wherein a second impurity selected from CF$_3$C≡CH, HFO-1243zf (CF$_3$CH═CH$_2$), HFO-1234ze (E/Z-CF$_3$CH═CHF), HCFO-1233zd (E/Z-CF$_3$CH═CHCl), HCFO-1233xf (CF$_3$CCl═CH$_2$) and combination thereof is additionally present.

6. The composition according to claim 3 wherein a second impurity selected from CF$_3$C≡CH, HFO-1243zf (CF$_3$CH═CH$_2$), HFO-1234ze (E/Z-CF$_3$CH═CHF), HCFO-1233zd (E/Z-CF$_3$CH═CHCl), HCFO-1233xf (CF$_3$CCl═CH$_2$) and combination thereof is additionally present.

7. The composition according to claim 6 wherein the second impurity is HFO-1243zf (CF$_3$CH═CH$_2$), HFO-1234ze (E/Z-CF$_3$CH═CHF), or HCFO-1233xf (CF$_3$CCl═CH$_2$).

8. The composition according to claim 1 additionally comprising a third halogenated impurity selected from the group consisting of HFO-1141 (CH$_2$═CHF), and HCFO-1131 (CH$_2$═CFCl and/or trans/cis-CHF═CHCl) and combination thereof, said third halogenated impurity and CH$_2$═CHCl being present in said composition in an amount greater than 0 ppm and less than or greater 50 ppm.

9. The composition according to claim 8 wherein said third halogenated impurity and CH$_2$═CHCl is present in said composition in an amount greater than 0 ppm and less than or greater 20 ppm.

10. The composition according to claim 8 wherein said third halogenated impurity and CH$_2$═CHCl is present in said composition in an amount greater than 0 ppm and less than or greater 10 ppm.

11. The composition according to claim 1 additionally comprising 1,3,3,3 tetrafluoro-1-propene.

12. The composition according to claim 8, wherein said third halogenated impurity is CH$_2$═CFCl.

13. The composition according to claim 11 wherein 1,3,3,3-tetrafluoro-1-propene is present in its Z-form.

14. The composition according to claim 11 wherein 1,3,3,3-tetrafluoro-1-propene is present in its E-form.

* * * * *